US007300926B2

(12) United States Patent
Prokai et al.

(10) Patent No.: US 7,300,926 B2
(45) Date of Patent: *Nov. 27, 2007

(54) STEROIDAL QUINOLS AND THEIR USE FOR ESTROGEN REPLACEMENT THERAPY (75) Inventors: Laszlo Prokai, Gainesville, FL (US); Katalin Prokai, Gainesville, FL (US); James Simpkins, Fort Worth, TX (US)

(73) Assignees: University of Florida Research Foundation, Inc., Gainesville, FL (US); University of North Texas Health Science Center at Fort Worth, Fort Worth, TX (US)

( * ) Notice: Subject to any disclaimer, the term of this patent is extended or adjusted under 35 U.S.C. 154(b) by 763 days.

This patent is subject to a terminal disclaimer.

(21) Appl. No.: 10/666,191

(22) Filed: Sep. 17, 2003

(65) Prior Publication Data
US 2004/0138190 A1     Jul. 15, 2004

Related U.S. Application Data (63) Continuation-in-part of application No. 10/405,413, filed on Apr. 1, 2003, now Pat. No. 7,026,306.

(60) Provisional application No. 60/369,589, filed on Apr. 1, 2002.

(51) Int. Cl.
A61K 31/56    (2006.01)
C07J 1/00     (2006.01)

(52) U.S. Cl. ....................... 514/178; 552/612

(58) Field of Classification Search ............. 552/612; 514/178
See application file for complete search history.

(56) References Cited

U.S. PATENT DOCUMENTS

| | | | |
|---|---|---|---|
| 2,910,486 A * | 10/1959 | Jiu ........................... | 552/612 |
| 2,950,291 A * | 8/1960 | Jiu ........................... | 552/613 |
| 5,108,996 A | 4/1992 | Claussner et al. | |
| 5,395,831 A | 3/1995 | Gemmill, Jr. et al. | |
| 5,552,395 A | 9/1996 | Gemmill, Jr. et al. | |
| 5,554,601 A | 9/1996 | Simpkins et al. | |
| 5,859,001 A | 1/1999 | Simpkins et al. | |
| 5,891,878 A | 4/1999 | Beasley et al. | |
| 6,197,833 B1 | 3/2001 | Simpkins et al. | |
| 6,319,914 B1 | 11/2001 | Simpkins et al. | |
| 6,583,170 B1 | 6/2003 | Pickar et al. | |
| 2003/0050295 A1 | 3/2003 | Pang | |
| 2003/0105167 A1 | 6/2003 | Dykens | |
| 2004/0214806 A1 | 10/2004 | Pang | |

FOREIGN PATENT DOCUMENTS

WO    WO 03/084978 A    10/2003

OTHER PUBLICATIONS

Numazawa et al., Chem. Pharm. Bull., 37(8), pp. 2058-2062, 1989.*
Ohe et al., Drug Metabolism and Disposition, 28(2), pp. 110-112, 2000.*
Nali et al., "The bis(salicylaldehyde)ethylenediiminocobalt (II) catalyzed C-10 oxygenation of estrogens.", J. of Molecular Catalysis, vol. 41(3), pp. 349-354, 1987, English Abstract only.*
Sedee et al., "A synthesis for p-quinol compounds from phenols fused with other saturated rings.", Tetrahedron Letters, vol. 24(51), pp. 5779-5780, 1983.*
Breuer, H. and Koster, G. (1974) "Interaction Between Oestrogens and Neurotransmitters at the Hypophysial-Hypothalamic Level." *Journal of Steroid Biochemistry*. vol. 5, pp. 961-967.
Galdecki, Z., P. et al. (1987) "Structure of 2,4-Dibromo-10β, 17β-dihydroxy-1,4-estradien-3-one" *Acta Cryst.* vol. c43, pp. 967-968.
Hiemke, C. et al. (1992) "Actions of Sex Hormones on the Brain." *Prog. Neuro-Psychopharmacol. & Biol.Psychiat.* vol. 16, pp. 377-388.
Kupfer, Rene, Long Yu Liu, Alban J. Allentoff, John A. Thompson (2001) "Comparisons of Hydroperoxide Isomerase and Monooxygenase Activities of Cytochrome P450 for Conversions of Allylic Hydroperoxides and Alcohols to Epoxyalcohols and Diols: Probing Substrate Reorientation in the Active Site" *Biochemistry* 40:11490-11501.
Liang, Y. et al. (2001) "Membrane fluidity effects of estratrienes." *Brain Research Bulletin*. vol. 54, No. 6, pp. 661-668.
McCullough, Louise D. and Patricia D. Hurn (Jul. 2003) "Estrogen and Ischemic Neuroprotection: an integrated view" *Trends in Endocrinology and Metabolism* 14(5):228-235.
Milic, D. et al.(1999) "X-Ray Crystal Structure of 10β-Hydroxy-4β,5β-expoxyerstr-1-en-3,17-dione and Antitumor Activity of its Congeners" *Molecules*, vol. 4, pp. 338-352.
Milic, D. et al. (1997) "The Synthesis and Biological Evaluation of A-Ring Substituted Steroidal *p*-Quinones" *Tetrahedron*, vol. 53, No. 41, pp. 14073-14084.
Milic, D. et al. (1997) "Structure and Reactivity of Steroidal Quinones" *J. Serb. Chem. Soc.*, vol. 62, No. 9, pp. 755-768.
Nilsen, J. and Brinton, D. (2003) "Divergent Impact of Progesterone and Medroxyprogesterone Acetate (Provera) on Nuclear Mitogen-activated Protein Kinase Signaling." vol. 100, No. 18, pp. 10506-10511.
Nilsen, Jon and Roberta Diaz Brinton (Jan. 2002) "Impact of Progestins on Estrogen-Induced Neuroprotection: Synergy by Progesterone and 19-Norprogesterone and Antagonism by Medroxyprogesterone Acetate" *Endocrinology* 143(1):205-212.

(Continued)

Primary Examiner—Barbara P. Badio
(74) Attorney, Agent, or Firm—Saliwanchik, Lloyd & Saliwanchik (57) ABSTRACT The present invention relates to novel estrogen-related steroidal quinols and their use as drugs for estrogen replacement therapy. The quinols of the present invention provide improved physicochemical properties, increased bioavailability, and improved distribution into tissues, bone, in the cardiovascular system, and in the CNS (central nervous system) with only a slight estrogenic action or no estrogenic action in the uterus. The compounds are suitable for the production of pharmaceutical agents for use in numerous indications (for example, estrogen replacement therapy, prevention and treatment of osteoporosis).

7 Claims, 4 Drawing Sheets

OTHER PUBLICATIONS

Numazawa, Mitsuteru, Kumiko Hoshi, Katsuhiko Kimura (1989) "Oxygenation of 2,4-Dibromoestrogens with Nitric Acid: A New Synthesis of 19-Nore Steroids" *Chem. Pharm. Bull.* 37(8):2058-2062.

Ohe, Tomoyuki, Masaaki Hirobe, Tadahiko Mashino (2000) "Novel Metabolic Pathway of Estrone and 17β-Estradiol Catalyzed by Cytochrome P-450" *Drug Metabolism and Disposition* 28(2):110-112.

Prokai, K. et al. (2003) "Modifying Peptide Properties by Prodrug Design For Enhanced Transport into CNS." *Progress in Drug Research*, vol. 61, pp. 158-188.

Prokai, L. et al. (2003) "Quinol-based Cyclic Antioxidant Mechanism in Estrogen Neuroprotection" *PNAS*, vol. 100 No. 2, pp. 11741-11746.

Prokai, L. et al. (2003) "Short Communication: Quinol-Based Metabolic Cycle For Estrogens in Rat Liver Microsomes" *Drug and Metabolism and Disposition*, vol. 31, No. 6, pp. 701-704.

Prokai, L. et al. (2001) "Synthesis and Biological Evaluation of 17β-Alkoxyestra-1,3,5(10)-trienes as Potential Neuroprotectants Against Oxidative Stress" *J. Med. Chem.*, vol. 44, pp. 110-114.

Prokai, L., et al. (2000) "Targeting Drugs to the Brain by Redox Chemical Delivery Systems" *Med. Res. Rev.*, vol. 20, No. 5, pp. 367-416.

Solaja, B. et al. (1996) "A Novel *m*-CPBA Oxidation: *p*-Quinols and Epoxyquinols from Phenols" *Tetrahedron Letters.* vol. 37, No. 21, pp. 3765-3768.

Beers, M.H. and R. Berkow, Editors, The Merck Manual of diagnosis and therapy, pp. 471-473 and pp. 1942-1944 (1999) Merck Research Laboratories, Whitehouse Station, N.J. USA.

Lupon, P. et al. (1983) "Photooxygenierung von Oestrogenen: Eine Neu 19-Norsteroid-Synthese" Verlagsgesellschaft, Weinheim, DE, vol. 95, No. 9, p. 757.

Sedee, A.G. J. et al. (1983) "A synthesis for p-quinol compounds from phenols fused with other saturated rings" *Tetrahedron Letters* 24(51):5779-5780.

\* cited by examiner

STEROIDAL QUINOLS AND THEIR USE FOR ESTROGEN REPLACEMENT THERAPY

CROSS REFERENCE TO RELATED APPLICATIONS

This application is a continuation-in-part of U.S. Ser. No. 10/405,413, filed Apr. 1, 2003, now U.S. Pat. No. 7,026,306; which claims the benefit of U.S. Provisional Application No. 60/369,589, filed Apr. 1, 2002.

GOVERNMENT SUPPORT

This invention was made with government support under a grant awarded from the National Institute of Neurological Disorders and Stroke under grant number NS44765, and a grant from the National Institutes of Health on Aging under grant number PO1 AG10485. The government has certain rights in the invention.

FIELD OF THE INVENTION

The present invention relates to the use of estrogen-related steroidal quinols for hormone replacement therapy. In particular, the present invention relates to methods of providing estrogen to a patient while minimizing the undesirable side effects associated with estrogen treatment or therapy, such as excessive estrogenic uterine stimulation.

BACKGROUND OF THE INVENTION

Menopause is a biological process in which a woman's ovaries reduce but do not completely stop their production of female sex hormones. Menopause is diagnosed when menstruation ceases permanently. Changing levels of female sex hormones that precede and postdate menopause often cause a variety of symptoms. Common health issues related to the menopausal transition and menopause include: irregular periods, hot flashes, increased risk of vaginal and/or bladder infection, urge incontinence, stress incontinence, fatigue, depression, loss of muscle mass, increased fat tissue, thinning and loss of skin elasticity, loss of bone tissue, impaired cognition, and an increased prevalence of cardiovascular disease.

One therapy used to combat symptoms associated with changing levels of female sex hormones is hormone replacement therapy (HRT). HRT is the administration of the female hormones including estrogen, progesterone, and androgens. One form of HRT is estrogen replacement therapy (ERT), which is the administration of estrogen alone. It is believed that HRT and ERT help in relieving symptoms of menopause and can be used to combat osteoporosis and to prevent the early onset of heart disease, two conditions often associated with post-menopause.

The use of HRT for bone loss prevention in post-menopausal women is well precedented. The normal protocol calls for estrogen supplementation using such formulations containing estrone, estriol, ethynyl estradiol, 17β-estradiol, esterified estrogens, or conjugated estrogens isolated from natural sources (i.e. PREMARIN conjugated estrogens from Wyeth-Ayerst) or synthetic estrogens. In some patients, ERT therapy may be contraindicated due to the proliferative effects of unopposed estrogens (estrogens not given in combination with progestins) have on uterine tissue. This proliferation is associated with increased risk for endometriosis and/or endometrial cancer. The effects of unopposed estrogens on breast tissue are less clear, but are of great concern to clinicians and patients alike.

Certain non-steroidal anti-estrogens have been shown to maintain bone mass in the ovariectomized rat model as well as in human clinical trials. Tamoxifen (sold as NOVADEX brand tamoxifen citrate by Zeneca Pharmaceuticals, Wilmington, Del.), for example, is a useful palliative for the treatment of breast cancer and has been demonstrated to exert an estrogen agonist-like effect on the bone, in humans. However, it is also a partial agonist in the uterus and this is cause for some concern. Raloxifene, a benzothiophene anti-estrogen, has been shown to stimulate uterine growth in the ovariectomized rat to a lesser extent than Tamoxifen while maintaining the ability to spare bone. A suitable review of tissue selective estrogens is seen in the article "Tissue-Selective Actions Of Estrogen Analogs", Bone Vol. 17, No. 4, October 1995, 181S-190S.

Further, the long term benefits of HRT and ERT remain questionable due to concerns regarding safety and efficacy. As noted above, HRT and/or ERT may increase an individual's risk of developing cancer. Specifically, it has been reported that prolonged exposure of the breast tissue to estrogen for five or more years of exogenous ERT is linked to an increased risk of breast cancer (Collaborative Group on Hormonal Factors in Breast Cancer, *Lancet*, 350:1047-1059).

Estrogens are degraded in the intestinal tract and rapidly metabolized by the liver. Specifically, estrogens undergo enterohepatic recirculation via sulfate and glucuronide conjugation in the liver, biliary secretion of conjugates into the intestine, and hydrolysis in the gut followed by reabsorption. The estrogen concentration encountered by the liver is generally four-fold to five-fold greater than estrogen levels in peripheral blood (the "first pass effect"). Administration of oral estrogens present high levels to the liver and may lead to an undesirable increase in the production of certain coagulation factors and renin substrates by the liver. Therefore, there is a need for therapeutic agents that are pharmaceutically effective at those regions where they are required.

An oral daily dose of 1 mg 17β-estradiol is considered to be equivalent, in terms of clinical efficacy, to biweekly 50 μg transdermal estradiol. This dose comparison may be misleading, however, because it does not account for large diffusion in estradiol metabolite concentrations nor does it account for the increase in sex hormone-binding globulin (SHBG) after oral, but not transdermal, ERT (Vehkavaara, S. et al., "Differential effects of oral and transdermal estrogen replacement therapy on endothelial function in postmenopausal women," *Circulation*, 102:2687-2693 (2000)). The long term consequences of this SHBG-binding variance has not been documented in clinical trials, but does account for many instances of 'non-response to adequate ERT' experienced by women in clinical practice.

Because of increased SHBG binding (and possibly other factors), more estrogen is needed after oral ERT to achieve a clinical response equivalent to that obtained by non-oral ERT. Only 5% of oral estradiol is bioavailable following the first-pass hepatic metabolism of oral estradiol. There is only minimal first-pass metabolism of non-oral estradiol (Kuhnz et al., "Pharmacokinetics of estradiol, free and total estrone, in young women following single intravenous and oral administration of 17 beta-estradiol," *Arzneimittelforschung*, 43:966-973 (1993)). Thus, high doses of estrogen are often necessary for adequate ERT. Unfortunately, such doses would have limited utility because of associated problems with toxicity and increased incidence of some forms of cancer. Therefore, the usefulness of such a method of treatment is quite limited.

A need exists for compositions and methods for administering estrogen-related quinols to individuals who require hormone replacement therapy. Furthermore, there exists a need for a therapeutically effective estrogen compound that retains its therapeutic activity while minimizing estrogenic proliferative effects in the uterus and breast.

BRIEF SUMMARY OF THE INVENTION

The present invention provides compositions and methods for the controlled administration of estrogen to patients requiring estrogen replacement therapy. In a preferred embodiment, the present invention provides estrogen-related steroidal quinols and their use as prodrugs to treat and/or prevent various symptoms and conditions associated with changing levels of female sex hormones.

In one aspect of the subject invention, estrogen-related steroidal quinols are administered to prevent bone loss in post-menopausal women. In further aspects of the invention, estrogen-related steroidal quinols are administered to mitigate the adverse effects associated with menopause.

In a preferred embodiment, the present invention provides inactive compounds that are converted in vivo into biologically active, therapeutic compounds by chemical or enzymatic transformation. The steroid-related quinols of the present invention are advantageous because they overcome problems associated with stability, toxicity, lack of specificity, and limited bioavailability, which may exist with the active form of the steroid. The quinols according to the present invention are particularly advantageous in minimizing the undesirable side effects associated with estrogen treatment or therapy, such as excessive estrogenic uterine or breast tissue stimulation.

As contemplated in the subject invention, an estrogen-related quinol can be rapidly converted to a biologically active estrogen compound via enzyme-catalyzed reduction that utilizes an endogenous reducing agent. The endogenous reducing agent may be, for example, the reduced forms of nicotinamide adenine dinucleotide (NADH) or nicotinamide adenine dinucleotide phosphate (NADPH). An advantage of the chemical conversion reaction is that the ensuing redox cycle does not generate reactive oxygen species that are detrimental to health.

In a specific embodiment, estrogen-related steroidal quinols that are related to a 10β-hydroxyestra-1,4-diene-3-one structure are administered to a patient requiring estrogen replacement therapy. Such quinols are advantageous because they can be converted in vivo into a parent phenolic A-ring estrogen, or estrogen analog compound, upon exposure to a reducing agent (i.e., endogenous NADPH) while minimizing undesirable side effects associated with estrogen treatment or therapy.

The present invention also concerns quinols having improved physiochemical properties when compared to lipophilic phenols such as estrogens and estrogen analogs. Advantageously, quinols of the invention demonstrate decreased lipophilicity. For preferred compounds of the subject invention there is a 10-fold to 50-fold decrease in the n-octanol/water partition coefficient (P) equivalent with ΔlogP of 1.0 to 1.7.

In addition, the present invention provides quinols having improved distribution into the central nervous system (CNS) as compared to lipophilic phenols such as estrogens and estrogen analogs. Further, the quinols of the invention demonstrate enhanced penetration across the blood-brain barrier.

The present invention also pertains to pharmaceutical compositions that comprise a therapeutically effective amount of one or more steroid-related quinols in pharmaceutical dosage form to treat and/or prevent conditions or symptoms associated with changes in estrogen level. Using the steroid-related quinols of the invention results in the reduction of peaks and troughs characteristic of dosing with a pharmaceutically active parent agent. Improved dose administrations result in the reduction of toxicity compared to the administration of active estrogen compounds. In addition, pharmaceutical compositions of the present invention have an increased therapeutic index compared to the active parent steroid while minimizing undesirable side effects associated with hormonal treatment or therapy, such as estrogenic uterine or breast tissue stimulation.

In another aspect, the present invention concerns therapeutic methods for the controlled administration to a patient of an effective amount of at least one or more of the steroid-related quinols described herein to provide estrogen replacement therapy.

DETAILED DISCLOSURE OF THE INVENTION

In accordance with the present invention, steroidal quinol compounds are administered to patients requiring estrogen replacement therapy. In particular, the present invention provides estrogen-related steroidal quinols and their use as prodrugs to treat and/or prevent conditions associated with changing levels of female sex hormones, i.e., menopause. The methods of the subject invention take advantage of the ability of steroidal quinol compounds to be converted in vivo into active estrogen-related steroidal compounds. In a preferred embodiment, the conversion of a steroidal quinol to a bioactive estrogen compound is performed via enzyme-catalyzed reduction. Thus, the administration of steroidal quinols as prodrugs is quite advantageous.

The present invention utilizes prodrug forms of estrogen and estrogen analogs which provide prolonged beneficial pharmaceutical effects, improved physicochemical properties, improved tissue distribution, increased bioavailability, resistance to metabolic inactivation, and reduced toxicity, in comparison to lipophilic, phenolic estrogens and estrogen analogs.

In contrast to the catechol structure of well-known phenolic estrogen products, steroidal quinols confer a non-aromatic nature to the steroidal A-ring. Thus, the biochemistry of steroidal quinols is substantially different from that of catechol estrogens to provide improved beneficial properties. In a particular embodiment, the estrogen-related steroidal quinols are non-aromatic until introduction to a chemical or enzymatic reductive aromatization process, which then converts the quinol into a bioactive, phenolic moiety that minimizes undesirable estrogenic effects. Thus, the steroidal quinol compound serves as a prodrug for active estrogens.

In a preferred embodiment, the present invention provides estrogen-related steroidal quinol compounds of the formula:

wherein

R is H, alkyl, cycloalkyl, aryl, heterocycle, heteroaryl, alkylamino, hydroxyalkyl, alkoxyalkyl or alkylaryl;

X is hydrogen, halogen, isopropyl, alkyl, alkenyl, alkynyl, carbocycle, cycloalkyl, aryl, heterocycle, heteroaryl, alkylamino, hydroxyalkyl, alkoxyalkyl, or a linear or branched hydrocarbon from 1-15 atoms carbon atoms in length, that can optionally include one or more heteroatoms in the chain;

Y is hydrogen, halogen, isopropyl, alkyl, alkenyl, alkenyl, carbocycle, cycloalkyl, aryl, heterocycle, heteroaryl, alkylamino, hydroxyalkyl, alkoxyalkyl, or a linear or branched hydrocarbon from 1-15 atoms carbon atoms in length, that can optionally include one or more heteroatoms in the chain; and Z is hydrogen, halogen, isopropyl, alkyl, alkenyl, alkynyl, carbocycle, cycloalkyl, aryl, heterocycle, heteroaryl, alkylamino, hydroxyalkyl, alkoxyalkyl, or a linear or branched hydrocarbon from 1-15 atoms carbon atoms in length, that can optionally include one or more heteroatoms in the chain.

In one embodiment, R is a straight or branched $C_{1-20}$ alkyl chain and X, Y, and Z are hydrogen. In yet another embodiment, X is hydrogen. In another embodiment, X and Y are hydrogen. In yet another embodiment, X and Z are hydrogen.

In a preferred embodiment, a patient requiring estrogen replacement therapy is administered steroidal quinol compounds of the formulae:

or

-continued wherein R is H or ethynyl.

The term "estrogen compound," as used herein, refers to estrogen; estrogen metabolites; estrogen analogs, antagonists, or modulators; and compounds with attributes that are categorized as similar or analogous to estrogen, estrogen metabolites, or estrogen analogs, antagonists, or modulators.

The term "patient," as used herein, describes an animal, including mammals, to which treatment with the compositions according to the present invention are provided. Mammalian species that benefit from the disclosed methods of treatment include, and are not limited to, apes, chimpanzees, orangutans, humans, monkeys; and domesticated animals (e.g., pets) such as dogs, cats, guinea pigs, and hamsters.

As used herein, the term "prodrug" denotes a molecule that is incapable of exerting the pharmacological activity of the active compound. The active compound will exert its therapeutic effects after it is bioactivated by a reducing agent. In accordance with the present invention, steroidal quinol compounds are administered as prodrugs to patients requiring estrogen replacement therapy. Under appropriate conditions, the steroidal quinol prodrugs of the invention are converted to therapeutically active estrogen compounds.

A variety of endogenous reducing agents are known and may be used to achieve preferential bioactivation (conversion) of the active compound of the invention within the body. Candidate reducing agents that could be utilized to activate the prodrugs of the invention include NADH or NADPH. As a result of the bioactivation, the quinol prodrugs are converted to an active phenolic estrogen or estrogen analog.

Figure 1:
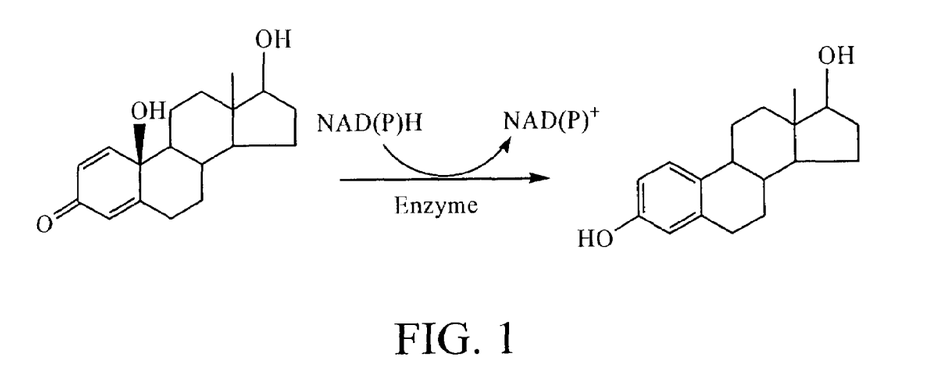
FIG. 1 illustrates the activation mechanism of the estrogen-related steroidal quinols of the present invention.

Estrogen-related steroidal quinols of the subject invention are advantageous as prodrugs because the steroidal quinol is reduced to an active estrogen by a reducing agent. An example of this process is shown in FIG. 1. As illustrated in FIG. 1, an estrone-quinol of the invention is converted to estrone by an enzyme-catalyzed reduction with NAD(P)H as a coenzyme. The estrone can then perform a variety of therapeutic functions including protecting cells against oxidative stress.

For estrogen replacement therapy, steroidal quinols can be used with pharmaceutically acceptable carriers, additives, or excipients, the proportions of which are determined by the solubility and chemical nature of the compound, chosen route of administration, and standard medical practice. In one embodiment of the present invention, pharmaceutical compositions include a therapeutically effective amount of any one or more of steroidal quinol compounds in pharmaceutical dosage form to treat and/or prevent symptoms, diseases, and disorders associated with changing levels of sex hormones. The therapeutically effective amount will vary with the condition to be treated, its severity, the treatment regimen to be employed, the pharmacokinetics of the agent used, as well as the patient treated.

The prodrug compounds of the subject invention can be formulated according to known methods for preparing pharmaceutically useful compositions. Formulations are described in a number of sources, which are well known and readily available to those skilled in the art. For example, *Remington's Pharmaceutical Science* (Martin E W [1995] Easton Pa., Mack Publishing Company, 19$^{th}$ ed.) describes formulations that can be used in connection with the subject invention. Formulations suitable for parenteral administration include, for example, aqueous sterile injection solutions, which may contain antioxidants, buffers, bacteriostats, and solutes, which render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Tissues that are protected by the use of the estrogen-related steroidal quinol compounds as prodrugs may be from children, adult or fetuses and include, but are not limited to, stem cells, blood and all of its components, including erythrocytes, leukocytes, platelets and serum, central nervous tissue, including brain and spinal cord tissue, neurons, and glia; peripheral nervous tissue, including ganglia, posterior pituitary gland, adrenal medulla, and pineal; connective tissue, skin, ligaments, tendons, and fibroblasts; muscle tissue, including skeletal, smooth and cardiac tissues or the cells therefrom; endocrine tissue, including anterior pituitary gland, thyroid gland, parathyroid gland, adrenal cortex, pancreas and its subparts, testes, ovaries, uterus, placenta, and the endocrine cells that are a part of each of these tissues; blood vessels, including arteries, veins, capillaries and the cells from these vessels: lung tissue; heart tissue and whole organ; heart valves; liver; kidney; intestines; bone, including osteocytes, osteoblasts and osteoclasts; immune tissue, including blood cells, bone marrow and spleen; eyes and their parts; reproductive tract tissues; or urinary tract tissue.

Examples of diseases, disorders and conditions that can be treated with the estrogen-related steroidal quinol compounds of the subject invention include: conditions, diseases, or symptoms associated with menopause, neurological and neurodegenerative diseases and conditions such as Alzheimer's disease, Parkinson's disease, amyotrophic lateral sclerosis (ALS), multiple sclerosis, peripheral neuropathy, shingles, stroke, traumatic injury, and various neurological and other degenerative consequences of neurological and chest surgeries, schizophrenia, epilepsy, Down's Syndrome, and Turner's Syndrome; degenerative conditions associated with AIDS; various bone disorders including osteoporosis, osteomyelitis, ischemic bone disease, fibrous dysplasia, rickets, Cushing's syndrome and osteoarthritis; other types of arthritis and conditions of connective tissue and cartilage degeneration including rheumatoid, psoriatic and infectious arthritis; various infectious diseases; muscle wasting disorders such as muscular dystrophy; skin disorders such as dermatitis, eczema, psoriasis and skin aging; degenerative disorders of the eye including macular degeneration and retinal degeneration; disorders of the ear such as otosclerosis; impaired wound healing; various cardiovascular diseases and conditions including stroke, cardiac ischemia, myocardial infarction, chronic or acute heart failure, cardiac dysrhymias, artrial fibrillation, paroxysmal tachycardia, ventricular fibrillation and congestive heart failure; circulatory disorders including atherosclerosis, arterial sclerosis and peripheral vascular disease, diabetes (Type I or Type II); various diseases of the lung disorders and diseases including lung cancer, pneumonia, chronic obstructive lung disease (bronchitis, emphysemia, asthma); disorders of the gastrointestinal tract such as ulcers and hernia; dental conditions such as periodontitis; liver diseases including hepatitis and cirrhosis; pancreatic ailments including acute pancreatitis; kidney diseases such as acute renal failure and glomerulonepritis; and various blood disorders such as vascular amyloidosis, aneurysms, anemia, hemorrhage, sickle cell anemia, autoimmune disease, red blood cell fragmentation syndrome, neutropenia, leukopenia, bone marrow aphasia, pancytopenia, thrombocytopenia, and hemophilia. The preceding list of diseases and conditions which are treatable according to the subject invention is not intended to be exhaustive or limiting but presented as examples of such degenerative diseases and conditions.

Pharmaceutical compositions based upon these estrogen-related steroidal quinol compounds may be formulated for a variety of routes of administration, including, for example, orally-administrable forms such as tablets, capsules or the like, or via parenteral, intravenous, intramuscular, transdermal, buccal, subcutaneous, suppository, or other route. In certain pharmaceutical dosage forms, certain of the present compounds may be more appropriate than other compounds, depending upon the route of administration and the targeted site within the patient.

Therapeutic methods according to the present invention include the controlled administration to a patient of an effective amount of at least one or more of the compounds as set forth above to provide estrogen replacement therapy. Administration to a patient may range from continuous (intravenous drip) to intramuscular, to several oral administrations per day (for example, Q.I.D.) and may include parenteral, including intravenous and intramuscular, oral, topical, subcutaneous, transdermal (which may include a penetration agent), buccal and suppository administration, among other routes of administration.

To prepare the pharmaceutical compositions according to the present invention, a therapeutically effective amount of one or more of the compounds according to the present invention is preferably intimately admixed with an optional pharmaceutically acceptable carrier according to conventional pharmaceutical compounding techniques to produce a dose. A carrier may take a wide variety of forms depending on the form of preparation desired for administration, e.g., oral or parenteral.

For parenteral formulations, the carrier may comprise sterile water or aqueous sodium chloride solution in combination with other ingredients that aid dispersion, such as ethanol and other pharmaceutically acceptable solvents. Of course, where solutions are to be used and maintained as sterile, the compositions and carrier must also be sterilized. Injectable suspensions may also be prepared, in which case appropriate liquid carriers, suspending agents and the like may be employed.

In preparing pharmaceutical compositions in oral dosage form according to the present invention, any one or more of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, tablets or capsules may be enteric-coated or sustained release by standard techniques.

The estrogen-related steroidal quinols of the present invention may be prepared using known reagents and reactions, including for example, oxidation of estradiol or estrone with tallium trifluoroacetate, lead tetraacetate, para-nitroperoxybenzoic acid, photooxygenation, or the like. The following Examples 1-6 are exemplary and provided for purposes of illustration and are not intended to be limitative.

Example 1 is a preparatory scheme for steroidal quinol compounds according to the present invention.

EXAMPLE 1

Synthesis of Estrone-Quinol By Transforming Phenol-to-Quinol

As understood by the skilled artisan, 10β-hydroxyestra-1,4-diene-3,17-dione (estrone-quinol) of the invention may be synthesized using a "one-pot" phenol-to-quinol transformation. The synthesis method utilizes meta-chloroperbenzoic acid (m-CPBA) as an oxidant, and dibenzoyl peroxide [$(PheCO)_2O_2$] as a radical initiator and visible-light irradiation that, in refluxing aprotic solvent, produces excellent yields of the quinols of the present invention.

By way of example, Milic et al., Tetrahedron Letters, 37:21, 3765-3768 (1996) disclose a "one-pot" method for synthesizing estrone-quinol. Oxidation of estrone to synthesize 10β-hydroxyestra-1,4-diene-3,17-dione is performed by heating a stirred solution of estrone (10.00 g, 37.0 mmol), meta-chloroperoxybenzoic acid (m-CPBA) (22.53 g, 111.0 mmol; 85% Jansen Chimica), and $(PheCO)_2O_2$ (900 mg, 3.70 mmol) in 2 L mixture of $CCl_4/Me_2CO$ (4/1) to reflux for 3 hours while irradiated with a 60 Watt tungsten lamp. Upon evaporation of the solvent, extraction is performed with $CHCl_3$ (3×200 mL), washing with $NaHCO_3$ (2×100 mL) and $H_2O$ (100 mL), and drying over anhydrous $Na_2SO_4$. The residue is then chromatographed on $SiO_2$ column. Elution may be performed with PhMe/EtOAc (1/1 and 7/3, respectively) and crystallization from benzene produces 5.19 g (49%) of estrone-quinol as colorless needles.

Data regarding the resulting estrone-quinols, as observed by Milic et al. are as follows: mp=219-221° C. (benzene); Lit.[4]=215-217° C.; [α]24.0 546=+62, [α]24.0 578 =+68 (c=1.32, chl.); UV:λMeOH max=229 nm (15500); IR(KBr): 3359x, 2941m, 1736s, 1664s, 1622s, 1601m $cm^{-1}$; $^1H$ NMR (250 MHz, DMSO-$d_6$): 7.13 (d, j=10.4 Hz, H—C(1)), 6.07 (dd, J=10.4, 2.4 Hz, H—C(2)), 5.92 (irreg. T, $J_{4,2}$=2.4, $J_{4,6\beta}$=1.2 Hz, H—C(4)) 5,67 (s, H-o, exchangeable with $D_2O$), 2.67 (tdd, J=15.2, 6.4, 1.2 Hz, $H_\beta$—C(6)), 1.97-1.83 (m, $H_\beta$—C(8) and $H_\beta$—C(11)-from NOE DIFF. Spectrum), 1.30-1.18 (m, $H_\beta$_C(11)), 0.97 (s, $H_3C$—C(13)); $^{13}C$ NMR (62.9 MHz, DMSO-$d_6$): 220.33 (C(17)), 185.53 (C(3)), 165.09 (C(5)), 150.25 (C(1)), 128.30 (C(2)), 123.09 (C(4)), 70.10 (C(10)), 51.18 (C( )), 50.10 (C(14)), 47.75 (C(13)), 35.62 (C(16)), 34.58 (C(8)), 32.19 (C(7)), 31.80 (C(6)), 31.03 (C(11)), 22.00 (C(12)), 21.90 (C(15)), 13.73 (C(18)); MS (EI, m/z): 286($M^+$, 84), 268($M^+-H_2O$, 39), 150(68), 145(100), 124(75), 107(50), 91(50), 79(54), 55(60); Anal. Calcd. for $C_{18}H_{22}O_3$ (286.37): C, 75.50; H. 7.74; Found: C=75.41, H=7.76.

Melting points were determined on a Boetius PMHD apparatus and were not corrected. Specific rotations were measured on a Perkin-Elmer 141 MC and Karl Zeiss Polamat A polarimeters at the given temperatures. IR spectra were recorded on Perkin-Elmer spectrophotometer FT-IR 1725X. UV spectra were recorded on a Beckman DU-420 spectrophotometer. $^1H$ NMR spectra were recorded on a Bruker AM-600, Bruker AM-250 and Varian Gemini-200 (at 600, 250, and 200 MHz, respectively) spectrometers. 2D and $^{13}C$ NMR spectra were recorded on a Bruker AC-250 spectrometer (at 62.9 and 250 MHz) in the indicated solvent using TMS as internal standard. Chemical shifts are expressed in ppm (δ) values and coupling constants (J) in Hz. Mass spectra were taken on a Finnigan-MAT 8230 spectrometer. The mention of specific instruments, instrument settings, and chromatographic media are for the purposes of example and not intended to be limiting.

Numerous other quinols for phenolic estrogens or estrogen analogs according to the present invention, as well as related, equivalent compounds, may be readily synthesized by analogy by simply modifying the above-described synthetic pathways, utilizing methods that are known to those of ordinary skill in the art.

The following Examples 2-5 describe experiments demonstrating the ability of the compounds of the present invention to be reduced into an active steroidal phenol structure.

EXAMPLE 2

In Vitro Study Demonstrating Estrogen-Receptor Binding Activity of the Steroidal Quinol of the Invention Competition binding assays were performed using an enzyme fragment complementation (EFC) method described in the HITHUNTER EFC Estrogen Chemiluminescence Assay kit (Fremont, Calif.). Competing ligands (estrone E1 and estrone-quinol E1-quinol) at final concentrations ranging from 10 pM to 10 µM were incubated with 5 nM recombinant estrogen receptor α (ERα) or estrogen receptor β (ERβ) (Panvera, Madison, Wis.) and 17β-estradiol-conjugated enzyme donor for 1.5 hours. The enzyme acceptor was then added for another 1.5 hours after which chemiluminescence substrate was added for another hour. Relative luminescences were determined using a Biotek FL600 plate reader (Biotek Instruments, Winooski, Vt.). Sigmoidal standard curves were created by GraphPad Prism (version 3.02 for Windows, GraphPad Software, San Diego, Calif.) using a four-parameter logarithmic curve to determine the concentration to reach 50% inhibition ($IC_{50}$). Similar procedures were also performed for estradiol (E2) and an estradiol-quinol (E2-quinol) of the invention. The results of the assays, as provided in the following Table 1, indicate that the estrone-quinols of the invention have no affinity ($IC_{50}$>10 µM) to estrogen receptors and thus, are not intrinsically feminizing and should not engender known undesirable side effects commonly associated with steroidal estrogens.

TABLE 1

| Estrogen-receptor binding affinity of phenolic A-ring steroids and their quinols | | | | |
|---|---|---|---|---|
| Estrogen Receptors | $IC_{50}$ (nM) | | | |
| (ER) | E2 | E2-quinol | E1 | E1-quinol |
| ERα | 1.3 | >10,000 | 6.1 | >10,000 |
| ERβ | 0.7 | >10,000 | 3.5 | >10,000 |

EXAMPLE 3

In Vitro Study Demonstrating the Reduction of Estrogen-Related Steroidal Quinol into an Active Structure Estrone-quinol (0.1 mM) was incubated at 37° C. in 0.1 M phosphate buffer pH 7.5 in the presence of 1 mM of NADH, NADPH, sodium ascorbate, and glutathione (GSH). Aliquots (500 µl) were taken after 60 minutes of incubation, and extracted with ethyl acetate (3×0.5 mL) and the mixture vortexed for 1 minute and centrifuged at 10,0000 rpm for 5 minutes. After removing the solvent, the residue of the combined organic extracts was analyzed for their estrone content by LC/MS/MS.

LC separation was done using a Supelco 5 cm×2.1 mm i.d. Discovery HS C-18 reversed-phase column with 0.25 mL/min water:methanol:2-propanol:acetic acid:dichloromethane (53:35:5:5:2, v/v) as a mobile phase. The sample residues were dissolved in 40 µl of mobile phase, respectively, and 5 µL of the solution was injected for analysis. Mass spectra were recorded on a quadrupole ion-trap instrument (LCQ, ThermoFinnigan) using positive-ion APCI as the method of ionization. MS/MS and $MS^3$ product-ion scans were obtained after collision-induced dissociation with helium as the target gas. Compound identification was based on retention time ($t_R$), APCI mass spectra, MS/MS and $MS^3$ with authentic compounds as references. Estrone, E1-quinol and 2-OH-estrone levels were determined by LC/APCI-MS/MS and calibration with solutions of known concentrations of the analytes extracted for analyses. As an internal standard, 1,3,5(10)-estratrien-17α-ethynyl-17β-ol (ethynylestradiol, Steraloids, Newport, R.I.) was added before each sample extraction.

Control incubations (0.1 mM estrone-quinol in 0.1 M phosphate buffer at pH 7.5 and 37° C. without the addition of a reducing agent were performed, as shown in FIG. 6, as well as incubation with GSH found to be free of estrone even after 12 hours. Trace amounts of estrone could be detected when the incubation was carried out in the presence of NADH and, especially, NADPH, as shown in FIGS. 7A and 7B.

EXAMPLE 4

In Vitro Reduction of an Estrogen-Related Steroidal Quinol Into an Active Steroidal Phenol Structure Estone was purchased from Steraloids Inc. (Newport, R.I.). The estrone-quinol of the invention was prepared from the estrone by the method of Example 1 described above. Cytochrome P450 reductase (EC 1.6.2.4) and all other chemicals were obtained from Sigma-Aldrich Inc. (St. Louis, Mo.). Male rat liver microsomes (Sprague-Dawley strain, untreated) were purchased from XenoTech LLC (Kansas City, Kans.).

Estrone-quinol (0.1 mM) and 1.0 mM NADH, NADPH, sodium ascorbate, or GSH in 0.1 M sodium phosphate buffer (1 ml of final volume, pH 7.5) was incubated at 37° C. At incremental time points, 100-µ aliquots were removed into ice-cooled centrifuge tubes, and 50 µl of glacial acetic acid was added. After immediate extraction with ethyl acetate (2×500 µl), the organic layer was evaporated under nitrogen stream at room temperature. Reconstitution of the samples with the LC mobile phase was followed by LC/MS analyses. For control, no reducing agents were used.

The incubation mixture (final volume 1 ml) containing 0.4 mM of $NADP^+$, 60 mM of KCl, 4 mM of $MgCl_2$, 4 mM of G-6-P, 5 U of G-6-P dehydrogenase, and 0.1 mM of estrone quinol of the invention in sodium phosphate buffer (pH 7.5) was preincubated for 2 minutes at 37° C. before microsomes (1 mg/ml protein) and 0.4 U of cytochrome P450 reductase (Roy and Liehr, 1988) were added. After 2.5 minutes of incubation, aliquots (100 µl) were taken, and glacial acetic acid (50 µl) was added to stop the reaction. To the mixture, ethyl acetate (3×500 µl, vortexed for 1 minute, centrifuged at 10,000 rpm for 5 minutes) was added. The organic layers were removed and combined followed by evaporation under nitrogen stream. The residue was dissolved in the mobile phase for LC/MS analysis. LC separation was performed using a 5 cm×2.1 mm i.d. Discovery HS $C_{18}$ reversed-phase column (Supelco, Bellefonte, Pa.) with 0.25 ml/min water/methanol/2-propanol/acetic acid/dichloromethane (53:35:5:5:2, v/v) as a mobile phase, respectively, and 5 µl of the solution was injected for analysis. Mass spectra were recorded on a quadrupole ion-trap instrument (LCQ; ThermoFinnigan, San Jose, Calif.) using positive-ion APCI as the method of ionization. MS/MS and $MS^3$ product-ion scans were obtained after collision-induced dissociation with helium as the target gas. Comparison with authentic reference compound (retention time, $t_R$, and mass spectra) was used for unambiguous identification of estrone.

As an internal standard, 1,3,5(10)-estratrien-17α-ethynyl-17β-ol (0.3 µM) was added before each sample extraction. Levels of estrone and the estrone-quinol of the invention were determined by LC/APCI-MS/MS and calibration with solutions of known concentrations of estrone (0.02 to 11 µM) and estrone-quinol (0.2 to 125 µM) extracted for analyses. The chromatographic peak areas for estrone, estrone-quinol, and the internal standard were obtained from m/z 271→253, m/z 287→269, and m/z 279→133+159 MS/MS transitions, respectively. Kinetic analysis of the microsomal metabolism was done by nonlinear curve-fitting (Scientist for Windows; MicroMath, Inc., Salt Lake City, Utah) presuming consecutive first-order processes in the cascade of estrone-quinol→estrone→estrone-metabolites.

Figures 2A, 2B:
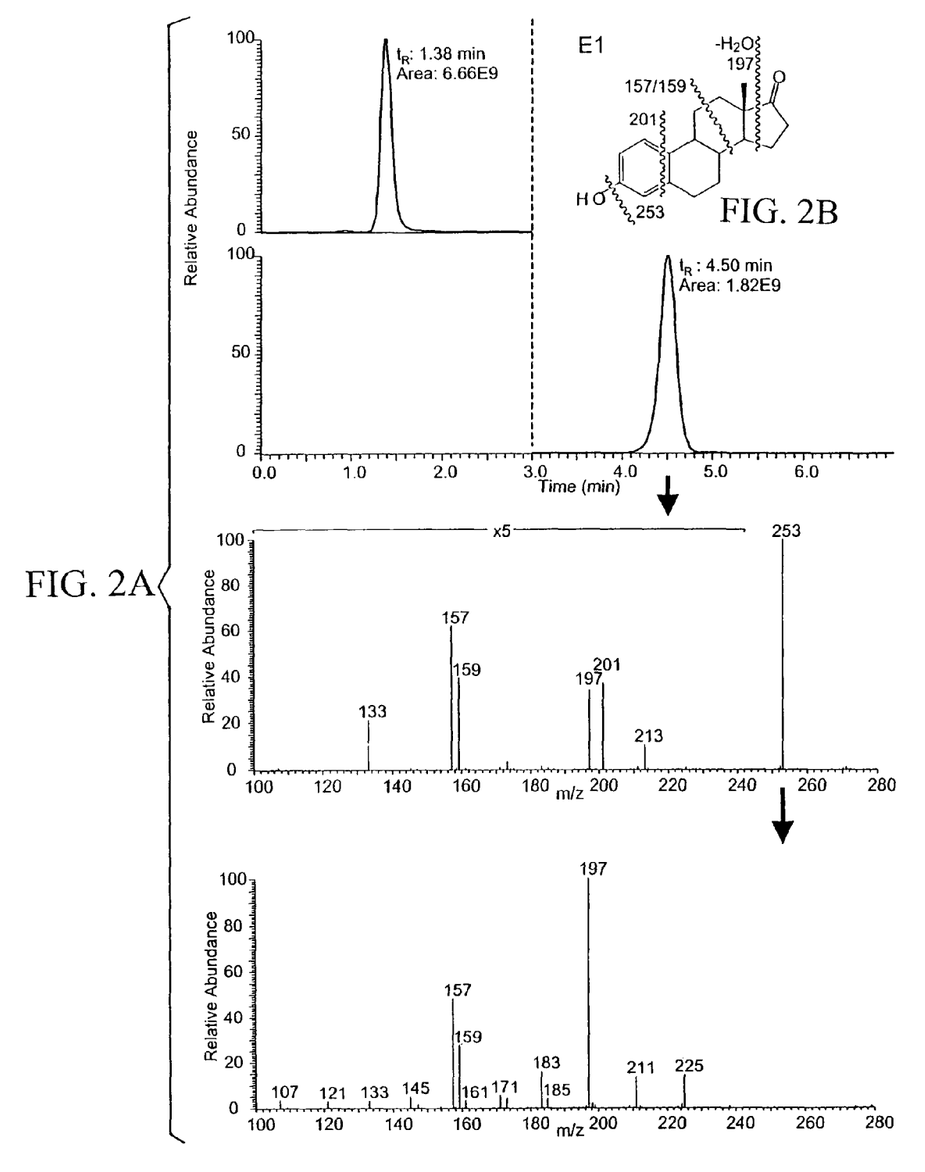
FIGS. 2A and 2B illustrate the chromatographic traces for the analytes, estrone and estrone-quinol, and in NADPH, and LC/APCI-MS/MS and MS$^3$ analyses demonstrating the reduction of estrone-quinol to estrone by NADPH, respectively.

Ass shown in FIGS. 2A and 2B, among the tested endogenous reducing agents, NADH and especially NADPH produced a significant extent of reductive conversion. Enzymes available in rat liver microsomes further catalyzed this reaction with 6.5±1.5 nmol $min^{-1}$·(mg of protein)$^{-1}$ measured as the initial rate of estrone formation at 37° C., whereas the initial rate of second-order reaction for the reduction of E1-quinol by a 10-fold excess of NADPH in a microsome-free buffer solution and under identical incubation conditions was 0.62±0.03 nmol·$min^{-1}$.

EXAMPLE 5

In Vivo Experiment Demonstrating the Reduction of an Estrogen-Related Steroidal Quinol into an Active Phenol Steroidal Structure Cerebral microdialysis experiments were performed to establish that estrone-quinol undergoes reduction to estrone in neuronal cells in vivo.

Male, Sprague rats (300-400 g) were anesthetized, placed in a stereotaxic instrument, and a guide cannula (CMA/12 guide cannula) was implanted into the ventral hippocampus under aseptic conditions. The guide cannula was fixed to the skull, together with stainless steel screws attached into additional two holes, with dental acrylics. Before starting the experiment (usually 5-7 days after the implantation of the guide cannula implantation) the rats were placed in a containment unit (BAS, Inc.) for at least 30 minutes. Then a microdialysis probe (CMA/12 polycarbonate membrane diameter 0.5 mm; membrane length 4 mm; molecular cut off: 5,000 Da) was inserted into the ventral hippocampus through the guide cannula. After insertion, the microdialysis probe was perfused with an artificial cerebrospinal fluid (aCSF) at a flow rate of 1 µl/min. maintained by a microperfusion pump (BAS BeeStinger) attached to the probe via polyethylene tubing and a liquid swivel. After equilibration for 50 minutes, an automatic refrigerated fraction collector (BAS HoneyComb) was used for continuous sampling of the probe efflux for 24 hours in 60 minute fractions collected into 300-µl glass vials (control). The artificial cerebrospinal fluid was then replaced by a perfusion solution containing 10 picomole/µL of estrone-quinol in aCSF (By measuring the decrease in the concentration of compound from the perfused solution, estrone-quinol entered the brain with a flux of about 2 picomole/minute). The sample collection was continued for another 24 hours. For LC/APCI-MS/MS analysis, 50 µL each from 20 fractions (1 mL total volume) of the control and the estrone-quinol microdialysis experiments, respectively, were combined and extracted with ethyl acetate after the addition of the internal standard.

Figure 3A:
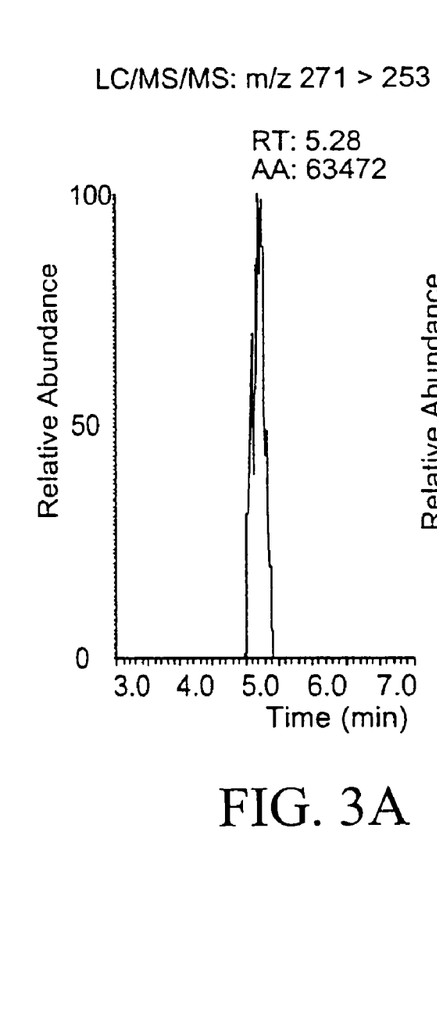
FIGS. 3A and 3B illustrate the LC/APCI-MS/MS analysis of the ethyl acetate extract from the in vivo cerebral microdialysate obtained after probe perfusion at 1 μL/minute with 10-picomole/μL of estrone-quinol artificial cerebrospinal fluid.
Figure 3B:
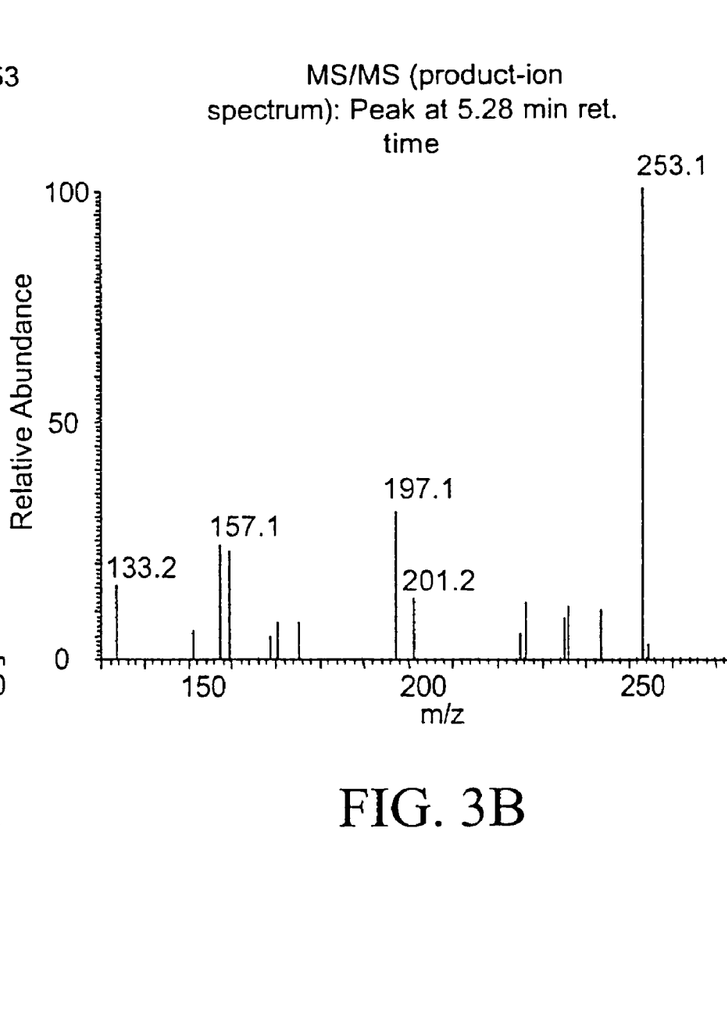
Figure 4:
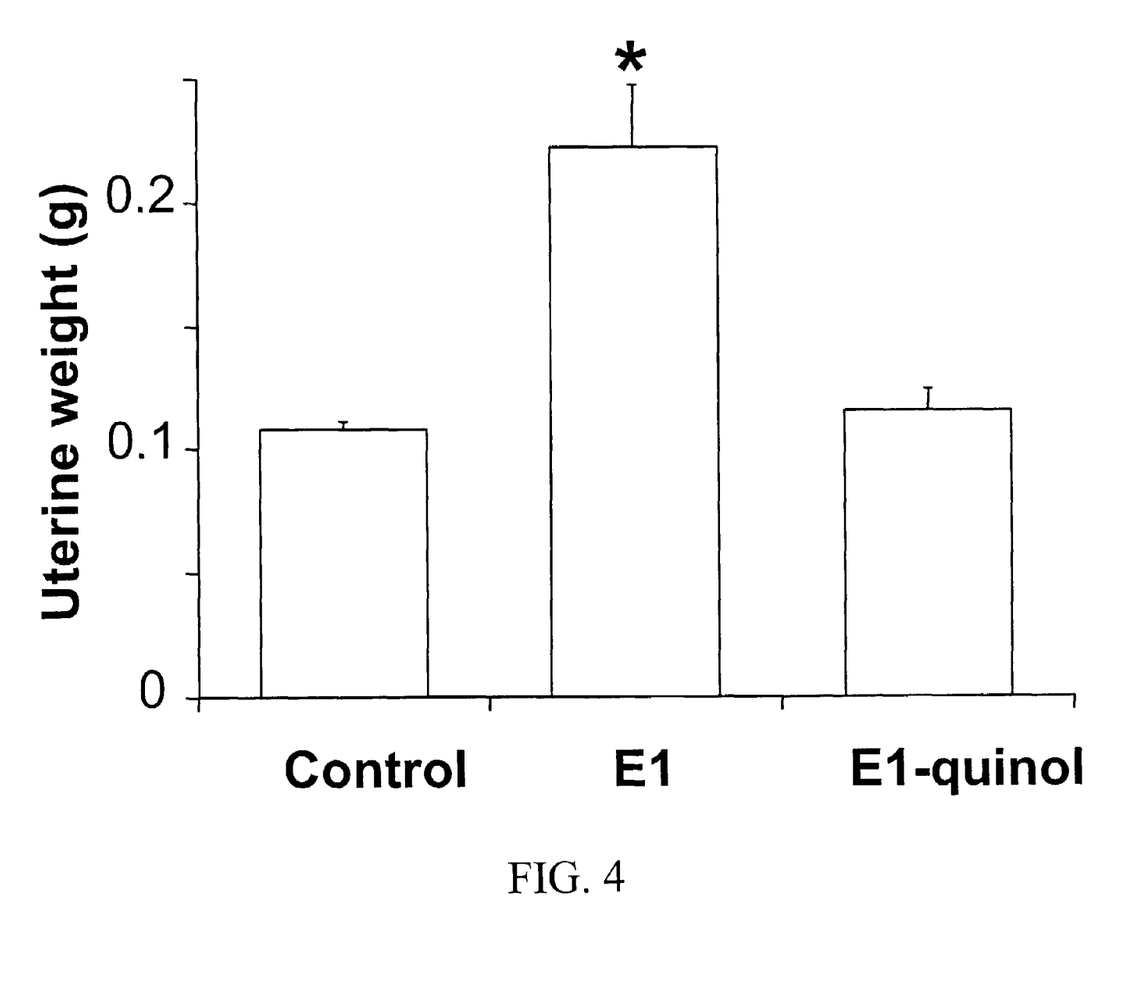
FIG. 4 illustrates the effect of the compounds of the subject invention on uterine weight.

Although estrone was not detectable in the control microdialysates, it was present in a detectable quantity in samples collected during the perfusion of the probes with the aCSF-solution containing estrone-quinol, as shown in FIGS. 3A and 3B. The chromatographic traces displayed the SRM m/z 287→m/z 269 SRM for estrone-quinol and m/z 271 m/z 253 for estrone. The peak at $t_R$=4.5 minutes was unequivocally identified, based on coelution with an authentic reference compound and identical APCI, MS/MS (given together with the origin of the major fragments observed) and $MS^3$ spectra, as estrone.

The following Example 6 describes an experiment that demonstrates the non-feminizing bioactivity (i.e., uterine weight gain) and effectiveness of the quinols of the present invention as compared to the phenolic estrogen compound.

EXAMPLE 6

In Vivo Demonstration of Minimized Side Effects of Uterine Weight Gain

Female, Sprague rats (200-250 g, Charles River, Wilmington, Mass.) were acclimatized for three days prior to surgery. Bilateral ovariectomy (OVX) was performed two weeks prior to middle cerebral artery occlusion (MCAO). Animals were anesthetized by intraperitoneal injection of ketamine (60 mg/kg) and xylazine (10 mg/kg). Rectal temperature was maintained at 37.5±0.5° C. during procedure. The middle cerebral artery was occluded for one hour then suture was withdrawn for reperfusion. Estrone and the estrone-quinol of the invention were dissolved in corn oil and administered at a dose of 200 µg/kg subcutaneously (sc) 2 hours prior to the onset of the one-hour MCAO. Animals were decapitated 24 hours after reperfusion. Uteruses were harvested, blotted, and weighed for comparison among treatment groups.

As summarized in Table 2 below and illustrated in FIG. 3, the uterine weight of the rats doubled in the group treated with estrone. In contrast, no difference in uterine weight was obtained from the control group when compared with the animals that received the estrone-quinol treatment of the invention.

TABLE 2

Uterine weights in Rats

| Compound administered to Rats | Number | Uterine Weight (g, ± SEM) |
|---|---|---|
| Control (OVX + vehicle) | 5 | 0.108 ± 0.003 |
| Estrone | 5 | 0.222 ± 0.022 |
| Estrone-quinol | 4 | 0.115 ± 0.010 |

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for providing estrogen replacement therapy to a patient while minimizing undesirable side effects associated with estrogen treatment or therapy, wherein said method comprises administering to the patient an effective amount of a quinol that is converted to a biologically active estrogen compound in vivo, wherein the quinol has the general structure:

wherein R is selected from the group consisting of H and ethynyl.

2. The method according to claim 1, further comprising administering the quinol by a route selected from the group consisting of oral, buccal, intramuscular, transdermal, intravenous, and subcutaneous.

3. The method according to claim 1, wherein the biologically active estrogen compounds are provided to the patient for the treatment of symptoms, diseases, or conditions associated with menopause, wherein the symptoms, diseases, or conditions associated with menopause is any one or more selected from the group consisting of: irregular period, hot flashes, increased risk of vaginal and/or bladder infection, urge incontinence, stress incontinence, fatigue, depression, loss of muscle mass, increased fat tissue, thinning and loss of skin elasticity, loss of bone tissue, and impaired cognition.

4. The method according to claim 1, wherein the biologically active estrogen compounds are provided to the patient for the treatment of conditions associated with the bone, wherein the conditions associated with the bone is any one or more selected from the group consisting of: osteoporosis, osteomyelitis, ischemic bone disease, fibrous dysplasia, rickets, Cushing's syndrome and osteoarthritis.

5. The method according to claim 1, wherein the biologically active estrogen compounds are provided to the patient for treatment of conditions associated with heart disease, wherein the conditions associated with heart disease is any one or more selected from the group consisting of: stroke, cardiac ischemia, myocardial infarction, chronic or acute heart failure, cardiac dysrhymias, artrial fibrillation, paroxysmal tachycardia, ventricular fibrillation and congestive heart failure.

6. A quinol that is converted to a biologically active estrogen compound via enzyme catalyzed reduction, said quinol having the general structure wherein
R is alkyl;
X is hydrogen;
Y is hydrogen; and
Z is hydrogen.

7. A pharmaceutical composition comprising a quinol that is converted to a biologically active estrogen compound via enzyme catalyzed reduction, wherein said composition further comprises a pharmaceutically acceptable carrier, wherein said quinol has the general structure:

wherein
R is alkyl;
X is hydrogen;
Y is hydrogen; and
Z is hydrogen.

* * * * *

UNITED STATES PATENT AND TRADEMARK OFFICE
CERTIFICATE OF CORRECTION

PATENT NO. : 7,300,926 B2 Page 1 of 1
APPLICATION NO. : 10/666191
DATED : November 27, 2007
INVENTOR(S) : Laszlo Prokai, Katalin Prokai and James W. Simpkins It is certified that error appears in the above-identified patent and that said Letters Patent is hereby corrected as shown below:

Column 5,
Lines 36, "alkyl, alkenyl, alkenyl," should read --alkyl, alkenyl, alkynyl,--.

Signed and Sealed this

Twenty-seventh Day of May, 2008

JON W. DUDAS
*Director of the United States Patent and Trademark Office*